United States Patent
Li et al.

(10) Patent No.: US 9,234,844 B2
(45) Date of Patent: Jan. 12, 2016

(54) CHLORIDE ION FLUORESCENCE DETECTION METHOD AND DEVICE, AND USE THEREOF

(71) Applicant: Shenzhen University, Shenzhen (CN)

(72) Inventors: Xuejin Li, Shenzhen (CN); Xiangzhong Ren, Shenzhen (CN); Zhuo Ni, Shenzhen (CN); Yiguang Wu, Shenzhen (CN)

(73) Assignee: Shenzhen University, Shenzhen, Guangdong Province (CN)

( * ) Notice: Subject to any disclaimer, the term of this patent is extended or adjusted under 35 U.S.C. 154(b) by 0 days.

(21) Appl. No.: 14/358,397

(22) PCT Filed: Oct. 31, 2012

(86) PCT No.: PCT/CN2012/083800
§ 371 (c)(1),
(2) Date: May 15, 2014

(87) PCT Pub. No.: WO2013/071822
PCT Pub. Date: May 23, 2013

(65) Prior Publication Data
US 2014/0315321 A1 Oct. 23, 2014

(30) Foreign Application Priority Data
Nov. 15, 2011 (CN) .......................... 2011 1 0361199

(51) Int. Cl.
*G01N 21/64* (2006.01)
*G01N 21/62* (2006.01)
(Continued)

(52) U.S. Cl.
CPC .......... *G01N 21/643* (2013.01); *G01N 21/7703* (2013.01); *G01N 21/77* (2013.01); *G01N 2021/6417* (2013.01); *G01N 2021/6439* (2013.01); *G01N 2021/6484* (2013.01); *G01N 2021/772* (2013.01);
(Continued)

(58) Field of Classification Search
CPC .. Y10T 436/19; Y10T 436/00; G01N 21/643; G01N 21/7703; G01N 21/77; G01N 21/75; G01N 21/6428; G01N 21/00; G01N 21/64; G01N 21/62; G01N 21/625; G01N 2021/6439
USPC ........................................................ 436/124
See application file for complete search history.

(56) References Cited

PUBLICATIONS

Nguyen, T. H. et al, Fiber Optic Chloride Sensor Based on Fluorescence Quenching of an Acridinium Dye, 2009, Proceedings of the SPIE—The International Society for Optical Engineering, Volu 7503, p. 750314-1 to 750314-5.*
(Continued)

*Primary Examiner* — Christine T Mui
(74) *Attorney, Agent, or Firm* — Novoclaims Patent Services LLC; Mei Lin Wong (57) ABSTRACT

A chloride ion fluorescence detection method and device, and a use thereof. The chloride ion fluorescence detection method utilizes chloride ions to influence luminescence characteristics of some photoluminescent substances to change the emission spectrum of the photoluminescent substances. The concentration of the chloride ions is detected through two processes comprising the fiber surface film forming and test liquid preparation of a fluorescent reagent sensitive to the chloride ions and measurement of information of fluorescence peak wavelengths or intensities. The method can be applied to the online assessment of the corrosion environment of steel bar concrete or the measurement of chloride ions in a laboratory.

12 Claims, 4 Drawing Sheets

(51) Int. Cl.
*G01N 21/00* (2006.01)
*G01N 21/77* (2006.01)

(52) U.S. Cl.
CPC ...... *G01N 2021/7786* (2013.01); *Y10T 436/00* (2015.01); *Y10T 436/19* (2015.01)

(56) References Cited

PUBLICATIONS

Zhang et al, Spectroscopy studies of methyl orange on silver colloids: pH and Cl-effects, Acta Physics Sinica, Jan. 2007, vol. 56, No. 1, pp. 170-177.*

* cited by examiner

CHLORIDE ION FLUORESCENCE DETECTION METHOD AND DEVICE, AND USE THEREOF

BACKGROUND OF THE PRESENT INVENTION

1. Field of Invention

The present invention relates to the technical field of photoelectric measurement, and more particularly to a method of fluorescence measurement of chloride ion, its device and use thereof.

2. Description of Related Arts

At present, there are different methods of chloride ion measurement. Existing method includes titration method with silver nitrate, ion chromatography method, volumetric method with silver nitrate solution, and etc. However, these methods have to be performed in a laboratory and cannot be used for on-site measurement. In addition, the testing object suitable for measurement is restricted. There is no practical and effective measurement method for chloride ion under specific conditions. For example, there is no such effective measurement method for chloride ion in reinforced concrete, the existence of chloride ion will have erosion effect on the reinforced concrete and adversely affect the durability of the reinforced concrete.

Accordingly, there is still room for improvement and development for the existing method of chloride ion measurement.

SUMMARY OF THE PRESENT INVENTION

In view of the above technical problems, an object of the present invention is to provide a method of fluorescence measurement for chloride ion, the device and application thereof in which characteristics of chloride ion on fluorescence of fluorescent substance is utilized to realize the measurement of chloride ion in order to solve the existing technical problems in chloride ion measurement.

According to the present invention, the foregoing and other objects and advantages are attained by the followings:

a method of fluorescence measurement for chloride ion, comprising the steps of: providing a fluorescent reagent and determining a chloride ion concentration of a test object through measuring the fluorescence spectrum of the fluorescent reagent, wherein the fluorescent reagent is a photoluminescence organic polymer material utilized for fluorescence measurement of chloride ion;

wherein the photoluminescence organic polymer material is sensitive to chloride ion, wherein optical properties of the photoluminescence organic polymer materials are changed after having interaction with chloride ions.

In the above method of fluorescence measurement for chloride ion, the fluorescent reagent is tetra(4,4',4'',4'''-N,N-diethylamino)tetraphenylethene quaternary ammonium salt compound, 5,15-bis[3-(2-(3-methylimidazolium)ethoxy)phenyl]zinc (II) porphyrin hexafluorophosphate, or a methyl orange-silver colloid system.

In the above method of fluorescence measurement for chloride ion, the method of fluorescence measurement of chloride ion comprises the steps of: covering a film of fluorescent reagent for chloride ion measurement onto an end surface of an optical fiber, placing the end surface of the optical fiber which is covered with the film of fluorescent reagent in a chloride ion testing environment, exciting the chloride ion sensitive materials on the end surface of the optical fiber by a light source through a coupling unit, placing the end surface of the optical fiber which is covered with the film of fluorescent reagent in the chloride ion testing environment, collecting the excited fluorescence light through the optical fiber and guiding the fluorescence light into a spectrum signal receiving unit through the coupling unit.

In the above method of fluorescence measurement for chloride ion, the method of fluorescence measurement for chloride ion comprises the steps of: preparing the fluorescent reagent into a fluorescent testing solution, placing the fluorescent testing solution into a testing container for chloride ion measurement, placing a test object into the testing container, exciting the fluorescent testing solution in the testing container by a light source through an optical fiber or through direct coupling, collecting the excited fluorescence light by the optical fiber and guiding the fluorescence light into a spectrum signal receiving unit through the coupling unit.

A device for fluorescence measurement of chloride ion comprises a light source, a coupling unit, a testing unit and a spectrum signal receiving unit; wherein the light source, the coupling unit and the testing unit are sequentially connected through an optical fiber, wherein the coupling unit and the spectrum signal receiving unit are connected through optical fiber;

wherein the testing unit comprises a fluorescent reagent for testing chloride ion, wherein the fluorescent reagent is photoluminescence organic polymer material which is sensitive to chloride ion and the optical properties of the photoluminescence organic polymer materials are changed after having interaction with chloride ions.

In the above device for fluorescence measurement of chloride ion, the testing unit is an optical fiber for testing of which an end surface of the optical fiber for testing is coated with a layer of fluorescent reagent in the form of a film for measurement of chloride ion.

In the above device for fluorescence measurement of chloride ion, the testing unit is a testing container which contains a fluorescent testing solution, wherein the fluorescent testing solution is a solution of fluorescent reagent for chloride ion measurement.

In the above device for fluorescence measurement of chloride ion, the fluorescent reagent is tetra(4,4',4'',4'''-N,N-diethylamino)tetraphenylethene quaternary ammonium salt compound, 5,15-bis[3-(2-(3-methylimidazolium)ethoxy)phenyl]zinc (II) porphyrin hexafluorophosphate, or a methyl orange-silver colloid system.

An application of the above device for fluorescence measurement of chloride ion includes an on-site analysis of erosion environment of reinforced concrete or chloride ion concentration measurement in a laboratory.

The present invention provides a method of fluorescence measurement of chloride ion, the device and application thereof in which the characteristic effect of chloride ion on the fluorescence of certain fluorescent substances is utilized to realize the measurement of chloride ion. According to the present invention, a fluorescent sensor is prepared by these fluorescent substances such that the concentration of chloride ion in a chloride ion existing environment can be measured. For example, through the measurement of chloride ion in the reinforced concrete structure, the erosion conditions of steel can be monitored for which the erosion rate and the erosion pattern can be determined, thereby the safety of the building structure can be ensured. Accordingly, the present invention provides very important theoretical significance and applied value.

DETAILED DESCRIPTION OF THE PREFERRED EMBODIMENT

The present invention provides a method of fluorescence measurement for chloride ion, the device and application thereof. The present invention is further described in details in the followings so as to illustrate the objectives and the technical features more clearly and explicitly. The following embodiments of the present invention are for the purpose of illustration only and are not intended to restrict the scope of the present invention.

According to the preferred embodiment of the present invention, the method of fluorescence measurement for chloride ion utilizes the characteristic of chloride ion in which the chloride ion is capable of affecting the fluorescence properties of certain fluorescent substances such that changes in the emission spectrum of the particular fluorescent substance is induced, therefore data such as the fluorescence peak wavelength or intensity can be utilized for chloride ion measurement. Accordingly, through the preparation of fluorescent sensor with these fluorescent substances, data such as concentration of chloride ion under environmental conditions with chloride ion can be measured.

The method of fluorescence measurement for chloride ion makes use of the characteristics of fluorescence spectrum of testing subject to determine the concentration of chloride ion in the testing subject in which the characteristics of fluorescence spectrum includes fluorescence intensity, wavelength, lifetime and etc. This method has a relatively high precision level and sensitivity and is convenience to use, that this method can be used under a laboratory condition or conducted under an on-site condition. This method is suitable for on-site analysis of erosion environment of reinforced concrete or for measuring concentration of chloride ion under the laboratory condition.

According to the preferred embodiment of the present invention, a particular photoluminescence polymer substance which is sensitive to chloride ion is selected. The specific optical properties of the polymer substance are induced to changes by the chloride ion after having interaction with the chloride ion. The changes in optical properties includes changes in characteristics of adsorption spectrum or emission spectrum. Another core feature is that the polymer substance can easily be coated onto the core of an optical fiber such that engineering application is facilitated.

According to the preferred embodiment of the present invention, a particular photoluminescence organic polymer substance is selected to use as a fluorescent reagent for fluorescence measurement of chloride ion. When the photoluminescence organic polymer substance is selected, not only the excellent photoluminescence properties of the substance are required, but also the sensitivity and selectivity to chloride ion, and the solubility in certain solvent to facilitate film formation on the surface of optical fiber are important factors for consideration.

The compound tetra(4,4',4",4'''-N,N-diethylamino)tetraphenylethene (TDETE) is a stilbene derivatives which is obtained by reductive coupling synthesis in which the two sides of the alkene double bond are bonded to four relatively large substituents, which is 4-N,N-dimethylaminophenyl. Tetra(4,4',4",4'''-N,N-diethylamino)tetraphenylethene (TDETE) reacts with iodomethane to form a quaternary ammonium salt compound with fluorescence characteristics and its molecular structure is shown in formula (I). TDETE quaternary ammonium salt compound belongs to a large p-bonding (conjugated) compound. When it is placed under an ionic environment, the chloride ion can partially substitute the iodide ion since the polarity of chloride ion is higher than the iodide ion, therefore the electron cloud distribution and the electronic energy level structure in the polymer are changed and the changes to the fluorescence spectrum and emission peak wavelength are induced.

Formula (I)

Figure 1:
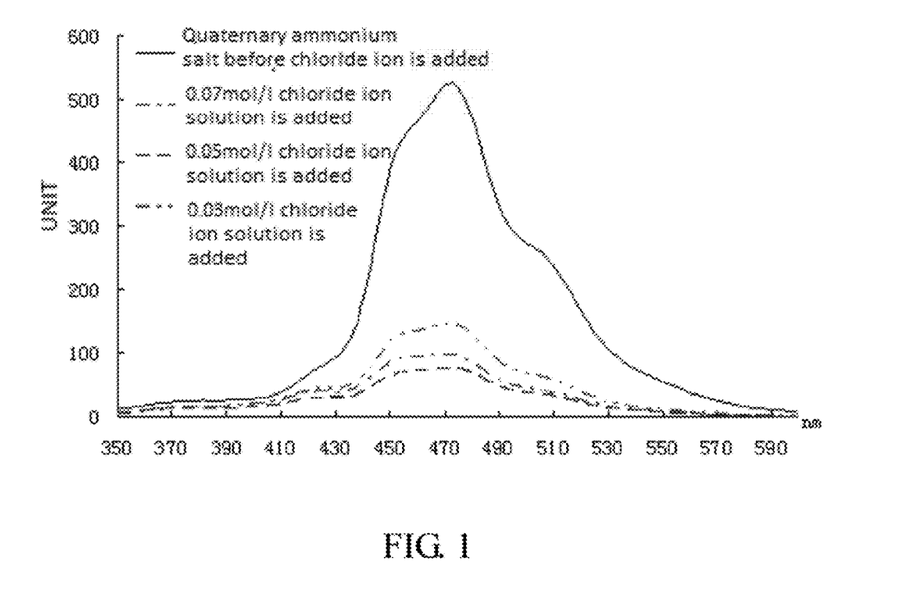
FIG. 1 is fluorescence spectra of tetra tetraphenylethene quaternary ammonium salt compound in chloride ion solution of different concentration respectively according to the preferred embodiment of the present invention.
Figure 2:
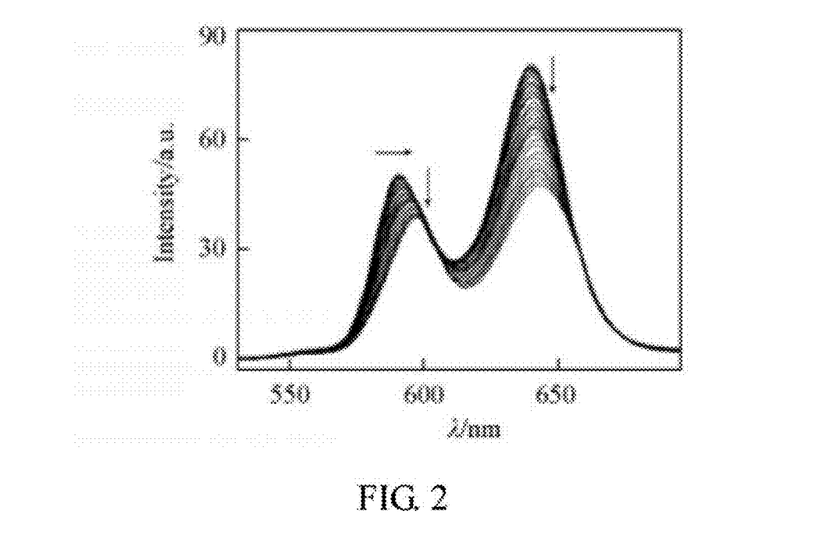
FIG. 2 is fluorescence comparison diagram of resulting solutions of 5,15-bis[3-(2-(3-methylimidazolium)ethoxy) phenyl]zinc (II) porphyrin hexafluorophosphate salt after interaction with chloride ion solution of different concentration respectively according to the preferred embodiment of the present invention.

Referring to FIG. 2 of the drawings, the changes in peak wavelength in the fluorescence emission band of TDETE quaternary ammonium salt compound at different concentration of chloride ion are illustrated. When the TDETE quaternary ammonium salt compound is placed under the chloride ion environment with concentration of chloride ion at 0.03 mol/L, 0.05 mol/L and 0.07 mol/L, its peak wavelength, which is originally 472.12 nm, is changed to 471.29 nm, 471.54 nm and 471.19 nm respectively, while its fluorescence intensity is lowered. The fluorescence intensity is correlated to the concentration of chloride ion. In addition, a new emission band is occurred between 392~428nm in the quaternary ammonium salt in chloride ion solution and the new emission band is directly proportional to the main emission band. Accordingly, TDETE quaternary ammonium salt compound is sensitive to chloride ion.

The present invention also provides 5,15-bis[3-(2-(3-methylimidazolium)ethoxy)phenyl]zinc (II) porphyrin hexafluorophosphate salt for use as the fluorescent reagent for fluorescence measurement of chloride ion.

Figure 3:
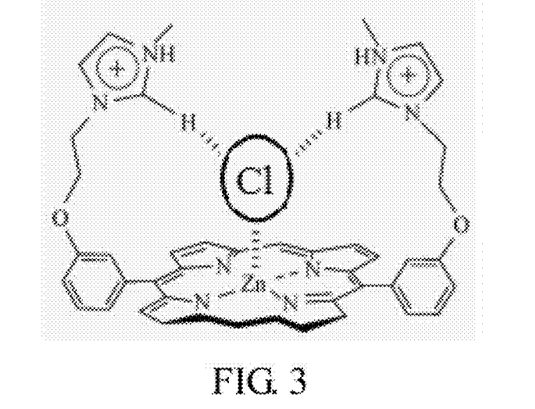
FIG. 3 is an illustration of occurrence of complexation action between 5,15-bis[3-(2-(3-methylimidazolium) ethoxy)phenyl]zinc (II) porphyrin hexafluorophosphate salt and chloride ion according to the preferred embodiment of the present invention.

5,15-bis[3-(2-(3-methylimidazolium)ethoxy)phenyl]zinc (II) porphyrin hexafluorophosphate salt is a porphyrin derivatives, which is a purple solid under room temperature and has a molecular structure as follows:

In general, porphyrin derivatives have strong fluorescence emission. The effect of chloride ion on 5,15-bis[3-(2-(3-methylimidazolium)ethoxy)phenyl]zinc (II) porphyrin hexafluorophosphate salt is that, when the concentration of chloride ion in acetonitrile solution is increased, the fluorescence intensity of porphyrin derivatives at 596 nm and 645 nm respectively are lowered significantly, which is shown in FIG. 2 of the drawings. The reason is that 5,15-bis[3-(2-(3-methylimidazolium)ethoxy)phenyl]zinc (II) porphyrin hexafluorophosphate salt shows supramolecular recognition of chloride ion through a three-points synergy: each of the two imidazole rings provides one activated C—H for hydrogen bond activity with anion [(C—H)$^+$—Cl$^-$], at the same time the zinc ion at the center of porphyrin ring functions as lewis acid and complexing action is occurred, which is shown as FIG. 3 of the drawings, thereby a supramoleucular complex is formed. In this supramoleucular system, effective electron/energy transfer between 5,15-bis[3-(2-(3-methylimidazolium)ethoxy)phenyl]zinc (II) porphyrin hexafluorophosphate salt and chloride ion is occurred, therefore the fluorescence intensity of porphyrin is reduced. Accordingly, 5,15-bis[3-(2-(3-methylimidazolium)ethoxy)phenyl]zinc (II) porphyrin hexafluorophosphate salt has significant linear response to interaction with chloride ion.

The present invention also provides methyl orange for use as the fluorescent reagent for fluorescence measurement for chloride ion. According to the preferred embodiment of the present invention, the nano silver particle in the methyl orange-silver colloid system has a large surface area with positive charge, therefore when the methyl orange which is an anionic dye is added to the silver colloid, the nano silver particle with positive charge and the —SO$_3^-$ group of methyl orange will attract each other due to Coulomb interaction. As a result, the dye molecules will longitudinally approaching the colloidal silver particles while the hydrophobic group (the dimethylamino group) at the opposite end of the methyl orange is induced towards the metal surface by action of water repulsion. Under the effect of electrostatic attraction and strong hydrophobic interaction at the metal surface, the methyl orange molecule is adsorbed onto the surface of metal particle and aggregate to form methyl orange-silver colloid nano particle. Since the silver particles have a spatial distribution of surface charge, the dye molecules are dispersedly adsorbed onto the surface of silver particles, which is shown in FIGS. 4(*a*) and (*b*) of the drawings.

Figure 4:
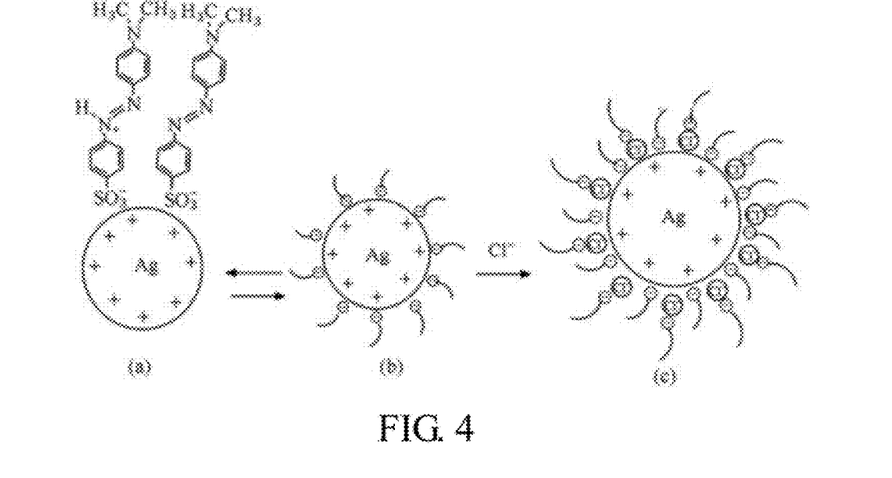
FIG. 4 is an illustration of a film structure model of methyl orange-silver colloid system and a tight adsorption model after chloride ion is added to the methyl orange-silver colloid system according to the preferred embodiment of the present invention.
Figure 5:
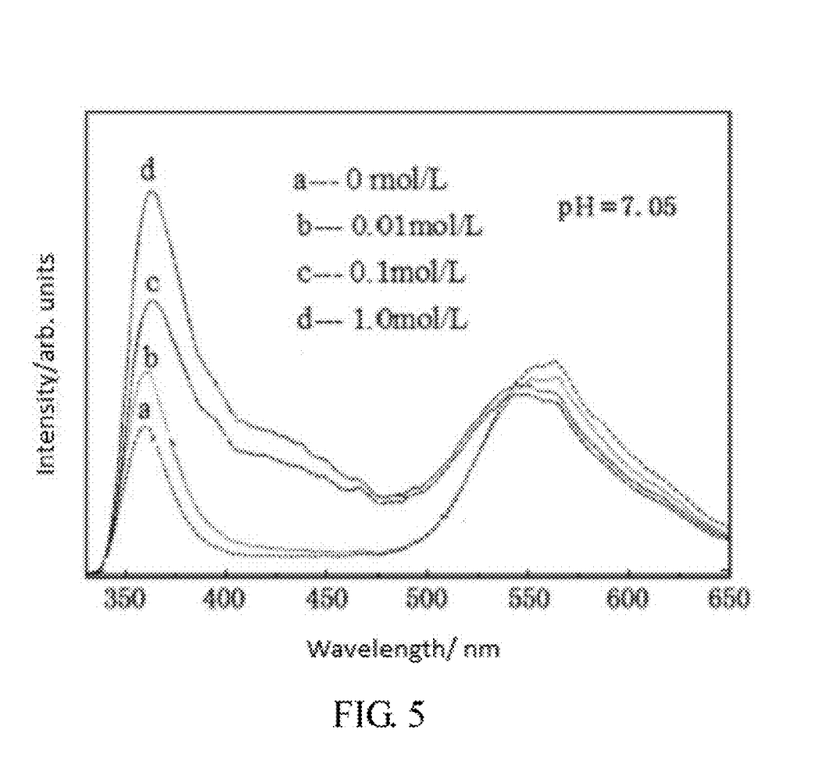
FIG. 5 is fluorescence spectra of methyl orange-silver colloid system in chloride ion solution of different concentration respectively according to the preferred embodiment of the present invention.

When chloride ion is added to the methyl orange-silver colloid system, the chloride ion is tightly adsorbed onto the colloidal silver surface, which is shown in FIG. 4(*c*) of the drawings. When the pH is smaller than 3.1, the chloride ion has promoting effect on adsorption and aggregation of molecule on the colloidal silver surface and affects the energy transfer efficiency. The addition of chloride ion will increase the aggregation and surface adsorption, and the effect of external solvent on this particular micro environment of aggregation surface will be reduced, when in turn causing the emission peak at 365 nm and 560 nm to have similar intensity and pattern when the pH is greater than 3.1. Also, the molecules which are tightly adsorbed on the silver particles will decrease the intensity of light incident on the silver particles, thus decreasing the energy transfer efficiency. Accordingly, the intensity of the characteristic photoluminescence emission peak at 560 nm is lowered after chloride ion is added. Meanwhile, as the level of intensity of adsorption is increased, the order of alignment of methyl orange is increased and the planarity and the rigidity of molecules will be increased, therefore the fluorescence peak intensity at 365 nm of π-π*transition associated molecules will be increased, which is shown in FIG. 5 of the drawings. Accordingly, it is determined that methyl orange-silver colloid system has a significant linear response to chloride ion in relation to fluorescence intensity of fluorescence spectrum at 365 nm.

Figure 6:
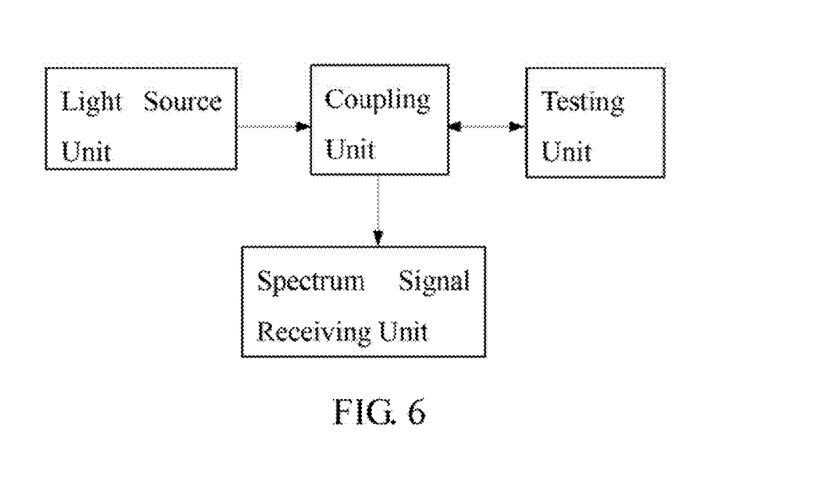
FIG. 6 is an illustration of a functional block diagram of the device for chloride ion measurement according to the preferred embodiment of the present invention.

According to the present invention, a measuring device for fluorescence measurement of chloride ion is provided, which is capable of utilizing a fluorescent reagent for chloride ion measurement for film formation onto a surface of fiber optics or for preparation of testing solution for measuring the concentration of chloride ion. As shown in FIG. 6 of the drawings, the measuring device for fluorescence measurement of chloride ion comprises a light source unit, a coupling unit, a testing unit and a spectrum signal receiving unit; the light source unit is arranged for light emission at a particular wavelength; and the testing unit is arranged for carrying the fluorescent reagent for chloride ion measurement. The light source, the coupling unit and the testing unit are sequentially connected through an optical fiber, the coupling unit device is connected to the spectrum signal receiving unit through an optical fiber. The testing unit contains the fluorescent reagent for chloride ion measurement in which the fluorescent reagent is a photoluminescence organic polymer substance which is sensitive to chloride ion such that its optical properties will be changed after having interaction with chloride ion.

Figure 7:
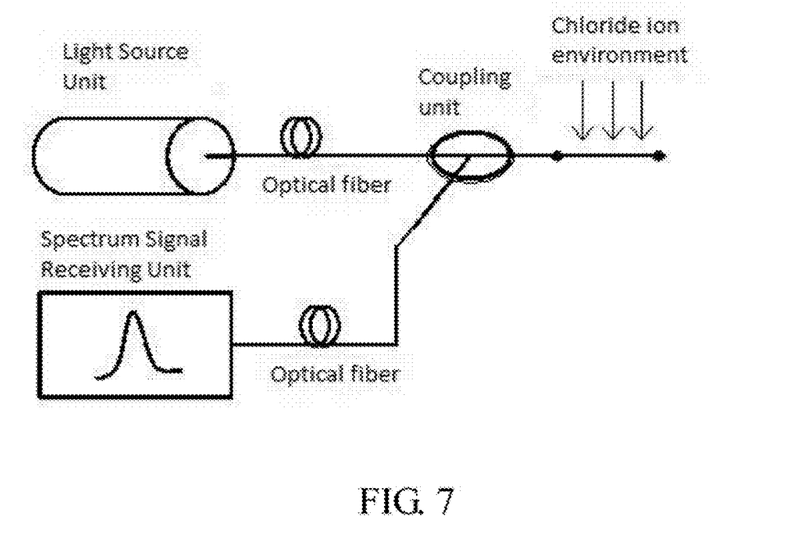
FIG. 7 is a structural illustration of the testing unit in the form of a chloride ion optical sensor according to the preferred embodiment of the present invention.

The testing unit can be in the form of an optical fiber for testing in which the optical fiber has one end providing an end surface for coating a layer of fluorescence film for chloride ion measurement. The fluorescent reagent is a photoluminescence organic polymer substance which is sensitive to chloride ion. The fluorescent reagent can be selected from tetra tetraphenylethene (chemical name tetra(4,4',4'',4'''-N,N-diethylamino)tetraphenylethene) quaternary ammonium salt compound, 5,15-bis[3-(2-(3-methylimidazolium)ethoxy) phenyl]zinc (II) porphyrin hexafluorophosphate salt or methyl orange-silver colloid system.

Referring to FIG. 7 of the drawings, the light source is arranged to excite the chloride ion sensitive materials on the end surface of the optical fiber through the coupling unit. The end surface of the optical fiber is placed in the chloride ion existing environment for testing, the excited fluorescence light is collected by the optical fiber and is guided into the spectrum signal receiving unit through the coupling unit.

Figure 8:
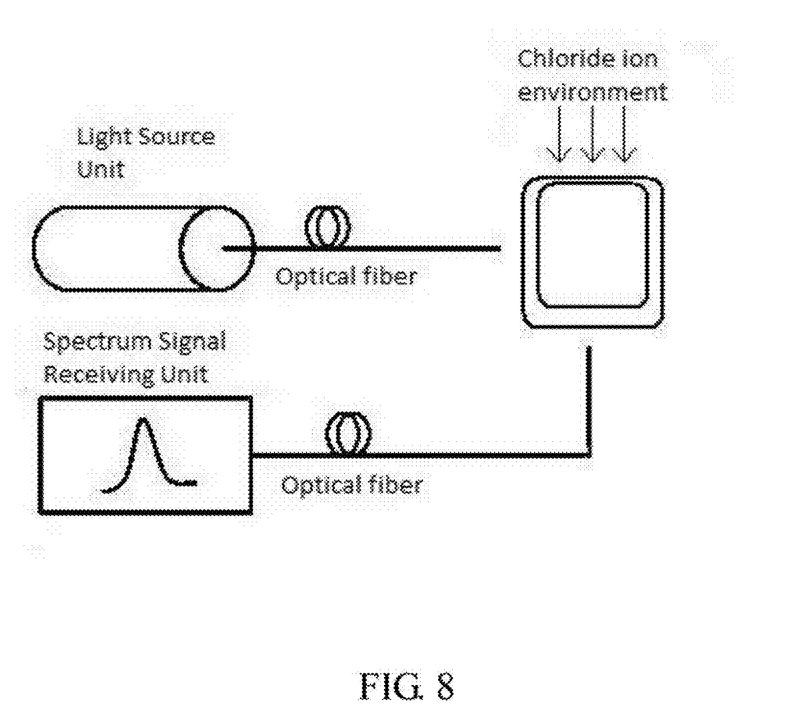
FIG. 8 is a structural illustration of the testing unit in the form of a fluorescent testing solution according to the preferred embodiment of the present invention.

The testing unit can be in the form of a testing container which contains a testing solution in which the testing solution is a fluorescent reagent for chloride ion measurement. The fluorescent reagent is a photoluminescence organic polymer substance which is sensitive to chloride ion. The fluorescent reagent can be selected from tetra tetraphenylethene (chemical name tetra(4,4',4",4'"-N,N-diethylamino) tetraphenylethene) quaternary ammonium salt compound, 5,15-bis[3-(2-(3-methylimidazolium)ethoxy)phenyl]zinc (II) porphyrin hexafluorophosphate salt or methyl orange-silver colloid system.

Referring to FIG. 8 of the drawings, the light source unit is coupled with the testing container for chloride ion directly or through an optical fiber to excite the fluorescent reagent for chloride ion measurement inside the testing container. The excited fluorescence light is then collected and guided into the spectrum signal receiving unit through the coupling unit. After that, through the changes in fluorescent spectrum characteristics, which includes fluorescent light intensity, wavelength and lifetime, the concentration of chloride ion in the test object is measured.

According to the present invention, a preparation process of coating a layer of fluorescent film for chloride ion measurement on the surface of optical fiber comprise the steps of:

stripping a coating layer and a cladding layer of the optical fiber;

uniformly mixing 0.1~30% by percentage weight of tetra tetraphenylethene quaternary ammonium salt compound or 5,15-bis[3-(2-(3-methylimidazolium)ethoxy)phenyl]zinc (II) porphyrin hexafluorophosphate salt with a film forming materials to form a mixture;

coating the mixture onto an end surface of the optical fiber and a core of the optical fiber such that a film is formed onto the surface of the optical fiber. The film forming materials can be selected from polyvinyl acetaldehyde, polyvinyl butyral, polyvinyl alcohol EG-40 or PVA-124. Alternatively, coating methyl orange-silver colloid onto an end surface of the optical fiber and a core of the optical fiber directly such that a film is formed onto the surface of the optical fiber.

Placing the end surface of the optical fiber which is coated with fluorescent reagent under a chloride ion environment for testing, collecting the fluorescence which is excited by the optical fiber, and guiding the fluorescent light into the spectrum signal receiving unit through the coupling unit. Then, measuring the concentration of the chloride ion in the test object through measuring the changes in the fluorescent spectrum characteristics which includes fluorescence light intensity, wavelength and lifetime.

According to the present invention, a preparation process of testing solution of fluorescent reagent for chloride ion measurement comprises the steps of:

Preparing a testing solution having a concentration of 0.1~30% by percentage weight of tetra tetraphenylethene (chemical name tetra(4,4',4",4'"-N,N-diethylamino)tetraphenylethene) quaternary ammonium salt compound, 5,15-bis[3-(2-(3-methylimidazolium)ethoxy)phenyl]zinc (II) porphyrin hexafluorophosphate salt or methyl orange-silver colloid system and placing into a testing container for chloride ion measurement.

The light source is coupled with the testing container for chloride ion measurement directly or through an optical fiber to excite the chloride ion sensitive materials inside the testing container for chloride ion measurement. The excited fluorescence light is then collected by the optical fiber and is guided into the spectrum signal receiving unit through the coupling unit. After that, through the changes in fluorescent spectrum characteristics, which includes fluorescence light intensity, wavelength and lifetime, the concentration of chloride ion in the test object is measured.

It is understood that the application of the present invention is not limited to the above exemplary embodiments. The person with ordinary skill in the art can modify or transform the present invention based on the above description and all such modifications and variations are within the scope of the present invention and are encompassed by the claims of the present invention.

What is claimed is:

1. A method of fluorescence measurement for chloride ion, characterized in that, the method comprises the steps of: providing a fluorescent reagent and determining a chloride ion concentration of a test object through measuring the fluorescence spectrum of the fluorescent reagent, wherein the fluorescent reagent is a photoluminescence organic polymer materials utilized for fluorescence measurement of chloride ion;

wherein the photoluminescence organic polymer materials is sensitive to chloride ion, wherein optical properties of the photoluminescence organic polymer materials are changed after having interaction with chloride ions, wherein the fluorescent reagent is tetra(4,4',4",4'"-N,N-diethylamino)tetraphenylethene quaternary ammonium salt compound, 5,15-bis[3-(2-(3-methylimidazolium) ethoxy)phenyl]zinc (II) porphyrin hexafluorophosphate, or a methyl orange-silver colloid system.

2. The method of fluorescence measurement for chloride ion according to claim 1, characterized in that, the fluorescent reagent is tetra(4,4',4",4'"-N,N-diethylamino)tetraphenylethene quaternary ammonium salt compound which has a highest peak and a characteristic peak pattern at 0.05 mol/L of chloride ion.

3. The method of fluorescence measurement for chloride ion according to claim 1, characterized in that, the method of fluorescence measurement for chloride ion comprises the steps of:

coating the fluorescent reagent for chloride ion measurement onto an end surface of an optical fiber directly for forming a film onto the optical fiber; placing the end surface of the optical fiber which is coated with the film of the fluorescent reagent in a chloride ion testing environment; exciting the fluorescent reagent which is a chloride ion sensitive materials on the end surface of the optical fiber by a light source through a coupling unit; placing the end surface of the optical fiber which is coated with the film of fluorescent reagent in the chloride ion testing environment; collecting fluorescence light which is excited by the light source through the optical fiber and guiding the fluorescence light into a spectrum signal receiving unit through the coupling unit.

4. The method of fluorescence measurement for chloride ion according to claim 2, characterized in that, the method of fluorescence measurement for chloride ion comprises the steps of:

preparing the fluorescent reagent into a fluorescent testing solution; placing the fluorescent testing solution into a testing container for chloride ion measurement; placing a test object into the testing container; exciting the fluorescent testing solution in the testing container by a light source through an optical fiber or through direct coupling method; collecting fluorescence light which is excited by the light source by the optical fiber and guiding the fluorescence light into a spectrum signal receiving unit through the coupling unit.

5. The method of fluorescence measurement for chloride ion according to claim 2, characterized in that, the method of fluorescence measurement for chloride ion comprises the steps of:

coating the fluorescent reagent for chloride ion measurement onto an end surface of an optical fiber directly for forming a film integrally onto the optical fiber; placing the end surface of the optical fiber which is coated with the film of the fluorescent reagent in a chloride ion testing environment; exciting the fluorescent reagent which is a chloride ion sensitive materials on the end surface of the optical fiber by a light source through a coupling unit; placing the end surface of the optical fiber which is coated with the film of fluorescent reagent in the chloride ion testing environment; collecting fluorescence light which is excited by the light source through the optical fiber and guiding the fluorescence light into a spectrum signal receiving unit through the coupling unit, thereby the optical fiber which is coated with the film of the fluorescent reagent can be placed into a gap within a reinforced concrete under an on-site condition for on-site analysis of erosion environment of reinforced concrete through measuring a concentration of chloride ion.

6. A device for fluorescence measurement of chloride ion, characterized in that, the device comprises a light source, a coupling unit, a testing unit and a spectrum signal receiving unit; wherein the light source, the coupling unit and the testing unit are sequentially connected through an optical fiber, wherein the coupling unit and the spectrum signal receiving unit are connected through optical fiber;

wherein the testing unit comprises a fluorescent reagent for chloride ion measurement, wherein the fluorescent reagent is photoluminescence organic polymer materials which is sensitive to chloride ion, and the optical properties of the photoluminescence organic polymer materials are changed in response to interaction with chloride ions, wherein the testing unit is an optical fiber for testing having an end surface coated with a layer of fluorescent reagent such that a film of the fluorescent reagent is formed on the end surface for measurement of chloride ion.

7. The device for fluorescence measurement of chloride ion according to claim 6, characterized in that, the testing unit is a testing container which contains a fluorescent testing solution, wherein the fluorescent testing solution is a solution of fluorescent reagent for chloride ion measurement, wherein the fluorescent reagent is tetra(4,4',4'',4'''-N,N-diethylamino)tetraphenylethene quaternary ammonium salt compound, 5,15-bis[3-(2-(3-methylimidazolium)ethoxy)phenyl]zinc (II) porphyrin hexafluorophosphate, or a methyl orange-silver colloid system.

8. The device for fluorescence measurement of chloride ion according to claim 6, characterized in that, the fluorescent reagent is tetra(4,4',4'',4'''-N,N-diethylamino)tetraphenylethene quaternary ammonium salt compound, 5,15-bis[3-(2-(3-methylimidazolium)ethoxy)phenyl]zinc (II) porphyrin hexafluorophosphate, or a methyl orange-silver colloid system.

9. An application of the device for fluorescence measurement of chloride ion according to claim 6, characterized in that, the device for fluorescence measurement of chloride ion is suitable for use under an on-site condition for on-site analysis of erosion environment of reinforced concrete for measuring a concentration of chloride ion.

10. An application of the device for fluorescence measurement of chloride ion according to claim 9, characterized in that, the fluorescent reagent is tetra(4,4',4'',4'''-N,N-diethylamino)tetraphenylethene quaternary ammonium salt compound, 5, 15-bis[3-(2-(3-methylimidazolium)ethoxy)phenyl]zinc (II) porphyrin hexafluorophosphate, or a methyl orange-silver colloid system.

11. An application of the device for fluorescence measurement of chloride ion according to claim 10, characterized in that, the fluorescent reagent is tetra(4,4',4'',4'''-N,N-diethylamino)tetraphenylethene quaternary ammonium salt compound which has a highest peak and a characteristic peak pattern at 0.05 mol/L of chloride ion.

12. The device for fluorescence measurement of chloride ion according to claim 7, characterized in that, the fluorescent reagent is tetra(4,4',4'',4'''-N,N-diethylamino)tetraphenylethene quaternary ammonium salt compound which has a highest peak and a characteristic peak pattern at 0.05 mol/L of chloride ion.

* * * * *